US010345214B2

(12) United States Patent
Coutard (10) Patent No.: US 10,345,214 B2
(45) Date of Patent: Jul. 9, 2019

(54) METHOD AND SYSTEM FOR ESTIMATING A CONCENTRATION OF A SPECIES IN A CULTURE MEDIUM BY LENSLESS IMAGING

(71) Applicant: Commissariat à l'énergie atomique et aux énergies alternatives, Paris (FR)

(72) Inventor: Jean-Guillaume Coutard, Saint Pancrasse (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 26 days.

(21) Appl. No.: 15/523,223

(22) PCT Filed: Oct. 30, 2015

(86) PCT No.: PCT/EP2015/075352
§ 371 (c)(1),
(2) Date: Apr. 28, 2017

(87) PCT Pub. No.: WO2016/066845
PCT Pub. Date: May 6, 2016

(65) Prior Publication Data
US 2017/0315041 A1 Nov. 2, 2017

(30) Foreign Application Priority Data

Oct. 31, 2014 (FR) ..................... 14 60494

(51) Int. Cl.
*G01N 15/06* (2006.01)
*G01N 15/02* (2006.01)
(Continued)

(52) U.S. Cl.
CPC .......... *G01N 15/06* (2013.01); *G01N 15/0211* (2013.01); *G01N 2015/0065* (2013.01);
(Continued)

(58) Field of Classification Search
CPC combination set(s) only.
See application file for complete search history.

(56) References Cited

U.S. PATENT DOCUMENTS 7,116,407 B2 * 10/2006 Hansen ............... G01N 15/147
356/73
8,455,258 B2 * 6/2013 Quake .................... B01D 57/02
436/63
(Continued)

FOREIGN PATENT DOCUMENTS

JP WO96/12962 * 5/1996 ........... G01N 33/555
WO WO-9612962 5/1996
(Continued)

OTHER PUBLICATIONS

International Search Report for PCT/EP2015/075352, dated Jan. 5, 2016.
(Continued)

*Primary Examiner* — Anand P Bhatnagar
(74) *Attorney, Agent, or Firm* — B. Aaron Schulman, Esq.; Stites & Harbison, PLLC (57) ABSTRACT

The method enables a concentration of a species in a culture medium (12) to be estimated using an estimation system (10) comprising a light source (16), a transparent substrate (14) and a matrix photodetector (18), the substrate being located between the source and the photodetector, the medium comprising biological particles (32) and changing color when said concentration varies. Said method comprises the following steps:—placing the medium on the substrate,—illuminating the medium via the light source,—acquisition of an image of the medium via the photodetector, each image being formed by a ray transmitted by the illuminated medium and comprising at least one diffraction pattern, each diffraction pattern corresponding to the waves diffracted by a biological particle when the medium is (Continued)

illuminated,—and calculating an estimate of said concentration as a function of a pixel intensity of the acquired image.

20 Claims, 4 Drawing Sheets

(51) Int. Cl.
    *G01N 15/14*             (2006.01)
    *G01N 15/00*             (2006.01)

(52) U.S. Cl.
    CPC ........... *G01N 2015/0233* (2013.01); *G01N 2015/0693* (2013.01); *G01N 2015/145* (2013.01)

(56) References Cited

U.S. PATENT DOCUMENTS

| | | | | |
|---|---|---|---|---|
| 8,592,215 B2* | 11/2013 | Quake | ............... | G01N 15/1459 436/53 |
| 9,994,889 B2* | 6/2018 | Tipgunlakant | ........... | C12Q 1/02 |
| 2003/0049693 A1* | 3/2003 | Goh | ............... | G01N 33/54373 435/7.9 |
| 2011/0151499 A1* | 6/2011 | Quake | ................ | B01D 57/02 435/29 |
| 2013/0074614 A1* | 3/2013 | Holmes | ............... | B01L 3/50825 73/864.01 |
| 2013/0078624 A1* | 3/2013 | Holmes | ................ | C12Q 1/00 435/6.11 |
| 2013/0079236 A1* | 3/2013 | Holmes | ................ | G01N 33/50 506/9 |
| 2014/0057255 A1* | 2/2014 | Holmes | ................ | G06F 19/366 435/6.11 |
| 2014/0273191 A1* | 9/2014 | Tipgunlakant | ........... | C12Q 1/02 435/288.4 |

FOREIGN PATENT DOCUMENTS

| | | |
|---|---|---|
| WO | WO-2008090330 | 7/2008 |
| WO | WO-2011049965 | 4/2011 |
| WO | WO-2014/009519 | 1/2014 |

OTHER PUBLICATIONS

Poher V et al: "Lensfree in-line holographic detection of bacteria", Advanced Microscopy Techniques II, SPIE, 1000 20th St. Bellingham WA 98225-6705 USA, vol. 8086, No. 1,Jun. 9, 2011(Jun. 9, 2011), pp. 1-7, XP060015100,DOI: 10.1117/12.889324 abstract figure 1.

\* cited by examiner

METHOD AND SYSTEM FOR ESTIMATING A CONCENTRATION OF A SPECIES IN A CULTURE MEDIUM BY LENSLESS IMAGING

FIELD OF THE INVENTION

The present invention relates to a method for estimating a concentration of a species in a culture medium. This detection method is implemented using an estimating system including a light source, a transparent substrate and a matrix photodetector, the transparent substrate being located between the light source and the matrix photodetector. The culture medium includes biological particles.

The invention also relates to a system for estimating the concentration of the species in the culture medium.

The invention in particular relates to the field of so-called lensless imaging, due to the absence of a lens focusing the light beam illuminating the transparent substrate.

BACKGROUND OF THE INVENTION

A lensless imaging system and an associated method making it possible to determine the position or the number of objects, such as cells, within the culture medium, are known from document WO 2008/090330 A1. The lensless imaging system is also used to track the movements of these objects and/or to detect a change of these objects, such as a cell division or an adhesion of cells to one another. This lensless imaging system then makes it possible to perform detecting, counting and tracking of cells in the culture medium.

However, such a lensless imaging system and such an associated method do not make it possible to observe other properties relative to the culture medium.

SUMMARY OF THE INVENTION

The aim of the invention is to propose a method and system for estimating a concentration of a species in the culture medium, by imaging without a lens.

To that end, the invention relates to a method for estimating a concentration of a species in a culture medium using an estimating system including a light source, a transparent substrate and a matrix photodetector, the transparent substrate being located between the light source and the matrix photodetector, the culture medium including biological particles and being able to change color when the concentration of the species varies, the method comprising the following steps:
placing the culture medium on the transparent substrate,
illuminating the culture medium using the light source,
acquiring an image of the culture medium using the matrix photodetector, each image being formed by a radiation transmitted by the illuminated culture medium and including at least one elementary diffraction pattern corresponding to waves diffracted by a biological particle when the culture medium is illuminated,
calculating an estimate of the concentration of the species in the culture medium from a pixel intensity of the acquired image.

Thus, the method according to the invention makes it possible to calculate an estimate of the concentration of the species in the culture medium based on a pixel intensity of the acquired image, the culture medium changing color when said concentration varies.

The invention generally relates to estimating concentrations of species in the culture medium which, when they vary, cause the color of the culture medium to change, the color change in some cases being obtained by introducing an associated reagent into the culture medium.

Species refers to a chemical species, in particular a molecule, such as a reactive oxygen species (ROS) or an ion, such as $H_3O^+$, $OH^-$, or a biological species, such as a cell, and in particular a live cell, or a protein. The estimate of the concentration of the species in the culture medium then corresponds to an estimate of a property of the culture medium. These properties are in particular the pH when the species is the $H_3O^+$ or $OH^-$ ion, a cell viability when the species is a live cell, a concentration of a reactive oxygen species. The concentration of a reactive oxygen species is sometimes likened to an oxidative stress of the culture medium. The invention then in particular relates to the field of immunocytochemistry (ICC).

Estimating the concentration in particular refers to calculating an estimated value of said concentration, or calculating a variation of said concentration, i.e., detecting an increase (positive variation, a decrease (negative variation) or an unchanged value (substantially zero variation) of said concentration.

According to other advantageous aspects of the invention, the estimating method comprises one or more of the following features, considered alone or according to all technically possible combinations:

the light source illuminates the transparent substrate directly, and the image is formed directly by the radiation transmitted by the illuminated transparent substrate, in the absence of a magnification lens positioned between the transparent substrate and the matrix photodetector;

the estimate of the concentration is an estimated value of said concentration;

the estimate of the concentration is an estimated variation of said concentration, said estimated variation being calculated by comparing the pixel intensity of the acquired image with that of a reference image, the reference image being chosen from among a predetermined image and an image of the culture medium previously acquired;

the concentration is chosen from among the group consisting of: the pH, a cell viability and a reactive oxygen species;

before the placement step, the method further comprises the following step: introducing a reagent into the culture medium to obtain the color change when the concentration varies;

after the acquisition step, the method further comprises the following steps:
identifying at least one elementary diffraction pattern in the acquired image, and
selecting pixels located outside each identified elementary diffraction pattern,
the estimate of the concentration of the species in the culture medium then being calculated, during the calculating step, from the intensity of the selected pixels;

after the acquisition step, the method further comprises the following step:
selecting a zone of interest in the acquired image,
the estimate of the concentration of the species in the culture medium then being calculated, during the calculating step, from the intensity of the pixels of the selected zone of interest, the selected zone of interest preferably including at least one elementary diffraction pattern;

the step for selecting the zone of interest is carried out prior to the identification step, the identification of the or each elementary diffraction pattern then being done in the selected zone of interest, the selection of the pixels situated outside each identified elementary diffraction pattern being done from among the pixels of the selected zone interest, and the estimate of the concentration of the species in the culture medium being calculated from the intensity of said selected pixels;

the method further comprises a preliminary calibration step, during which a relationship between the intensity of the concentration is determined using a calibration medium having a given value of the concentration, the calibration medium preferably having no biological particles;

during the calibration step, the value of the concentration of the species in the calibration medium is modified according to different successive values, and the relationship between the intensity and the concentration is determined for the different successive values;

before the acquisition step, the method further comprises the following step:
placing a filter between the matrix photodetector and the transparent substrate, the filter being able to transmit only a predefined range of wavelengths, the predefined range of wavelengths preferably being determined based on a predefined value of the concentration.

after the acquisition step, the method further comprises the following steps:
identifying at least one elementary diffraction pattern in the acquired image, and
determining a characteristic relative to each biological particle corresponding to a respective identified elementary pattern;

the intensity taken into account during the calculating step is a mean value or a median value of the intensity of the considered pixels; and the acquired image is monochromatic.

The invention also relates to a system for estimating a concentration of a species in a culture medium, the culture medium including biological particles and being able to change color when the concentration of the species varies, the system comprising:
a transparent substrate configured for receiving the culture medium,
a light source configured for emitting a light beam illuminating the culture medium,
a matrix photodetector configured for acquiring an image of the culture medium, each image being formed by a radiation transmitted by the illuminated culture medium and including at least one elementary diffraction pattern corresponding to waves diffracted by a biological particle when the culture medium is illuminated,
the transparent substrate being located between the light source and the matrix photodetector, and
an information processing unit configured for calculating an estimate of the concentration of the species in the culture medium from a pixel intensity of the acquired image.

BRIEF DESCRIPTION OF THE DRAWINGS

These features and advantages of the invention will appear upon reading the following description, provided solely as a non-limiting example, and done in reference to the appended drawings, in which.

DETAILED DESCRIPTION OF PREFERRED EMBODIMENTS

In the following of the description, the expression "substantially equal to" defines a relationship of equality to within plus or minus 10%, preferably to within plus or minus 5%.

Figure 1:
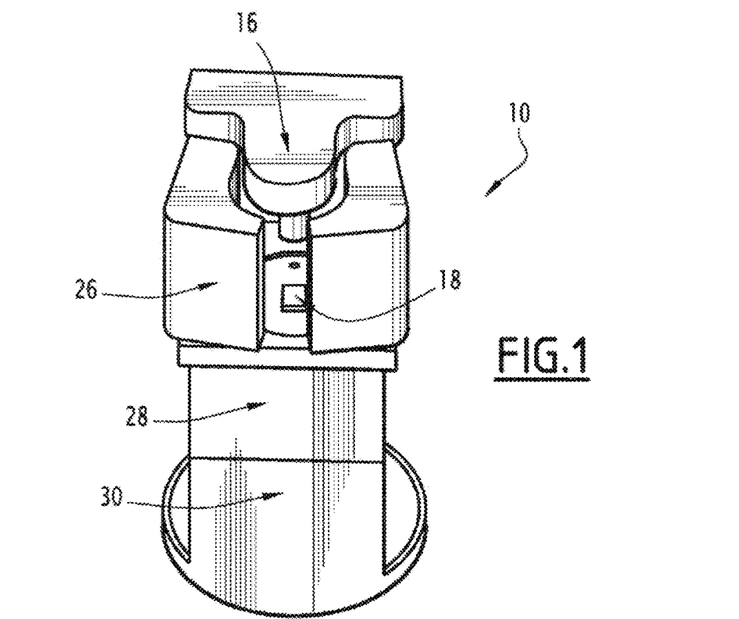
FIG. 1 is a perspective view of an estimating system according to the invention.
Figure 2:
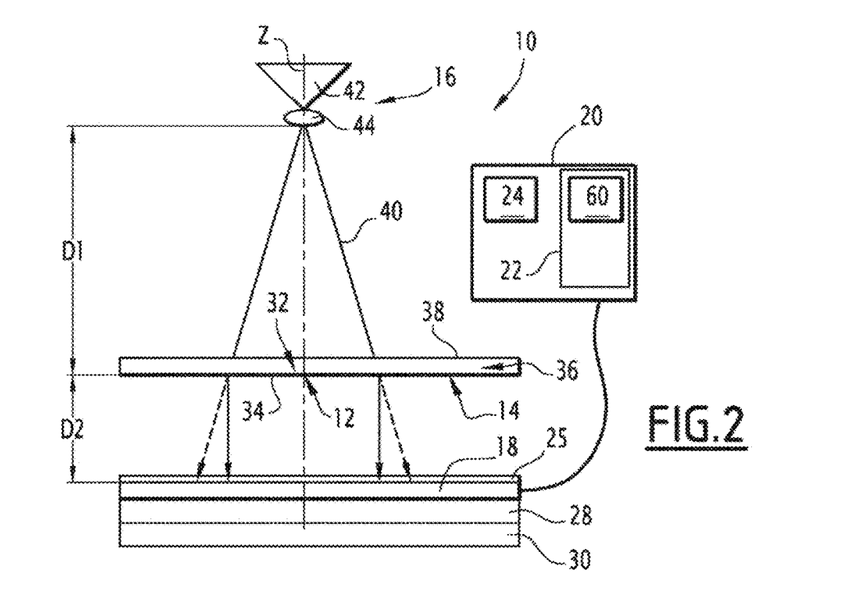
FIG. 2 is a schematic illustration of the estimating system of FIG. 1, the estimating system comprising a transparent substrate suitable for receiving the culture medium, a light source suitable for illuminating the culture medium, a matrix photodetector for acquiring images of the radiation transmitted by the illuminated medium and an information processing unit, the information processing unit being configured to calculate an estimate of the concentration of the species in the culture medium based on a pixel intensity of the acquired image, the culture medium changing color when said concentration varies.

In FIGS. 1 and 2, a system 10 for estimating a concentration of a species in a culture medium 12 comprises a transparent substrate 14 configured for receiving the culture medium 12. The estimating system 10 also comprises a light source 16 and a matrix photodetector 18 configured for acquiring several successive images $I_n$, $I_{n+1}$ of a radiation transmitted by the medium 12 illuminated by the light source 16.

The estimated concentration is for example the pH. Alternatively, the estimated concentration is a cell viability, i.e., a concentration of live cells, or a reactive oxygen species.

The estimating system 10 is generally configured for estimating said concentration associated with the culture medium 12 by lensless imaging, the matrix photodetector 18 not including a magnification lens.

The estimating system 10 also comprises an information processing unit 20, shown in FIG. 2, comprising a memory 22 and a processor 24 associated with the memory 22.

As an optional addition, the estimating system 10 comprises an optical filter 25 placed between the transparent substrate 14 and the matrix photodetector 18 in the vertical direction Z, the optical filter 25 for example being in contact with the matrix photodetector 18. The optical filter 25 is configured for transmitting only a predefined range of wavelengths. The predefined range of wavelengths is preferably determined based on a predefined value of the concentration.

As an optional addition, the estimating system 10 comprises a device 26 with swinging doors, the doors being painted black, making it possible to isolate the radiation transmitted by the illuminated medium 12 from the outside environment. The swinging door device 26 makes it possible, when the swinging doors are closed, for a technician to then operate in ambient light, but without disrupting the measurements done inside the estimating system 10.

The estimating system 10 also comprises a heat dissipater 28 and a fan 30 to regulate the temperature of the matrix photodetector 18, in particular to cool it in case of excessive heating. These elements are optional.

The culture medium 12 for example includes biological particles 32, i.e., cells (in particular blood cells, and for example white blood cells, red blood cells or platelets), bacteria or bacterial colonies, or cell aggregates. The culture medium 12 is for example made up of said cells. The biological particles 32 form diffracting particles that generally have a diameter smaller than 100 µm. The diameter of the biological particles 32 is for example comprised between 1 µm and 100 µm. The cells, such as the white blood cells and red blood cells, have a diameter of approximately 10 µm.

The culture medium 12 is able to change color when the concentration of the species in question varies.

As an optional addition, the color change of the culture medium 12 when the concentration of the species in question varies is obtained by introducing a suitable reagent into the culture medium 12. When the estimated concentration is the pH, the reagent is for example phenol red. When the estimated concentration is the cell viability, the reagent is for example methanethiosulfonate (MTS), (2,3-Bis-(2-Methoxy-4-Nitro-5-Sulfophenyl)-2H-Tetrazolium-5-Carboxanilide) (XTT), or a soluble salt of tetrazolium. When the estimated concentration is a concentration of a reactive oxygen species, for example hydrogen peroxide ($H_2O_2$), the reagent is for example (10-acetyl-3,7-dihydroxyphenoxazine), also called Amplex Red®.

The transparent substrate 14 is positioned between the light source 16 and the matrix photodetector 18, and is substantially perpendicular to a vertical direction Z corresponding to the illumination direction of the culture medium 12 by the light source 16, as shown in FIG. 2.

The transparent substrate 14 for example comprises a transparent slide 34. In this example, the transparent substrate 14 is placed at the bottom of a petri dish 36. The petri dish 36 here serves to confine the culture medium 12, and is optional. It is configured for being placed directly on the matrix photodetector 18. The petri dish 36 additionally includes a cover 38 in order to protect the culture medium 12.

The light source 16 is configured for emitting a light beam 40 in the vertical direction Z in order to illuminate the culture medium 12 including the diffracting particles 22.

The light source 16 is positioned at a first distance D1 from the transparent slide 34 in the vertical direction Z. The first distance D1 preferably has a value comprised between 1 cm and 16 cm, for example equal to 5 cm.

The light source 16 is preferably spatially coherent and preferably monochromatic. The term monochromatic designates a spectral width smaller than 80 nm, preferably smaller than 40 nm at mid-height.

The light source 16 for example includes a periodic source such as a light-emitting diode 42 (also called LED), and a diaphragm 44 placed in contact with the LED 42, as shown schematically in FIG. 2. The diaphragm 44 has a diameter comprised between 40 µm and 400 µm, preferably substantially equal to 150 µm. This makes it possible to increase the spatial coherence of the light radiation. The LED 42 for example has a wavelength substantially equal to 530 nm.

Alternatively, the light source 16 is made up of the light-emitting diode 42, and does not comprise a diaphragm. The light-emitting diode 42 then has sufficiently reduced dimensions to be considered spatially coherent, the diameter of the light-emitting diode 42 then for example being smaller than one tenth of the first distance D1.

Also alternatively, the light source 16 is a spatially and temporally coherent light source, for example a laser diode or a vertical cavity surface emitting laser (VCSEL).

The matrix photodetector 18 is configured for acquiring successive images of the radiation transmitted by the culture medium 12, containing the diffracting biological particles 22 and illuminated by the light beam 40. Transmitted radiation refers to the radiation passing through the culture medium 12 such that the matrix photodetector 18 and the light source 16 are situated on either side of the culture medium 12 including the diffracting particles 22.

The matrix photodetector 18 is a two-dimensional image sensor, i.e., in a plane substantially perpendicular to the vertical axis Z. The matrix photodetector 18 is a pixelated image sensor, for example a CMOS (Complementary Metal Oxide Semiconductor) sensor. Alternatively, the matrix photodetector 18 is a CCD (Charged-Coupled Device) sensor.

The matrix photodetector 18 includes a plurality of pixels, not shown, each having dimensions smaller than or equal to 10 µm. In the example of FIGS. 1 and 2, each pixel is in the shape of a square with each side substantially equal to 2.2 µm.

The matrix photodetector 18 may additionally include micro-lenses, not shown, each micro-lens being positioned above a corresponding pixel. Such micro-lenses are integrated into the sensor and make it possible to improve the collection performance, but without forming a magnifying lens positioned between the transparent substrate 14 and the photodetector 18.

The images acquired by the matrix photodetector 18 are formed by the radiation transmitted directly by the lit medium 12, in the absence of a magnifying lens positioned between the substrate 14 and the matrix photodetector 18. The photodetector 18 is also called a lens-free imaging device, and is able to form an image of the medium 12, while being placed at a small distance therefrom. A small distance refers to a distance smaller than several centimeters, preferably smaller than 1 cm. The photodetector 18 is positioned at a second distance D2 from the transparent slide 34 in the vertical direction Z, and the second distance D2 is then generally smaller than 5 cm, preferably substantially equal to 1 cm.

Favoring a small value for the second distance D2, i.e., a short distance between the matrix photodetector 18 and the transparent substrate 14, makes it possible to limit the interference phenomena between different diffraction patterns when the culture medium 12 is illuminated.

The matrix photodetector 18 is then configured for acquiring an image of at least one elementary diffraction pattern 50 transmitted by the culture medium 12, each elementary diffraction pattern 50 corresponding to waves diffracted by a diffracting particle 22 when the culture medium 12 is illuminated. Thus, the matrix photodetector 18 makes it possible to obtain an image $I_n$, called observed image, including one or several elementary diffraction patterns 50, where n is an index comprised between 1 and N and corresponding to the number of the image in the sequence of acquired successive images, with n and N integers greater than or equal to 1. The acquisition rhythm is generally comprised between 40 images per second and one image every 10 to 20 seconds.

The acquired images $I_n$, $I_{n+1}$ correspond to the interferences of diffraction patterns created by the particles 32 suspended in the culture medium 12. The illumination of the particles 32 by the spatially and temporally coherent beam 40, such as a laser beam, creates a diffraction pattern, which varies during the movement of the particles 32 contained in the medium 12.

The observation of a usable diffraction pattern, by placing the matrix photodetector 18 at such a small distance, is in particular due to the absence of a magnifying lens between the transparent substrate 14 and the photodetector 18.

Figure 4:
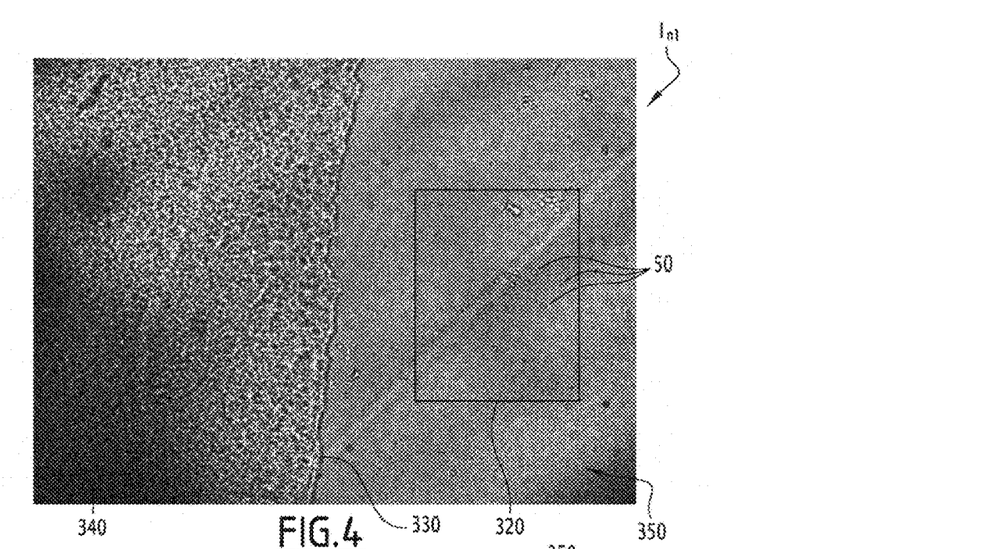
FIGS. 4 and 5 are views of images acquired at two separate moments in time using the photodetector of FIG. 2, during the illumination of the culture medium.
Figure 5:
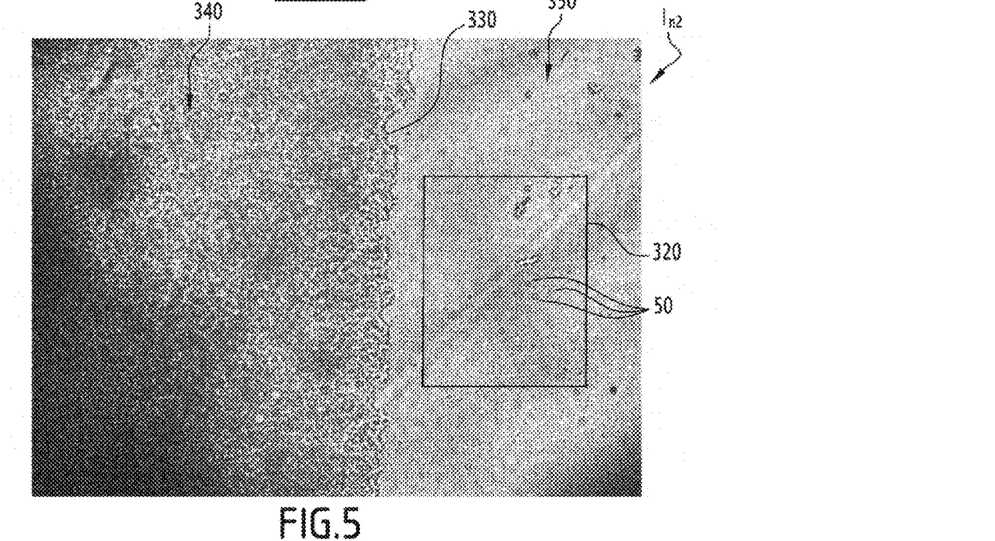

FIGS. 4 and 5 show two acquired images, each including a plurality of elementary diffraction patterns 50, each pattern 50 being made up of a central zone, the intensity of which is substantially homogenous, this central zone being surrounded by concentric rings, the intensity of which is alternately low (dark rings) and high (light rings).

Each image $I_n$ acquired by the matrix photodetector 18 includes a plurality of pixels $I_n(x,y)$, each being identified by an x-axis and a y-axis in the image, and the matrix photodetector 18 is configured for measuring the intensity $I(x,y)$ of each pixel. Each acquired image $I_n$ is for example monochromatic.

The memory 22 is adapted to store software 60 for estimating the concentration of the species in the culture medium 12.

The processor 24 is configured for running the estimating software 60.

The estimating software 60 forms means for estimating the concentration of the species in the culture medium 12.

Alternatively, the estimating means 60 are made in the form of a programmable logic component or in the form of a dedicated integrated circuit.

The estimating software 60 is configured to calculate an estimate of the concentration of the species in the culture medium from the pixel intensity of the acquired image.

The estimating software 60 is for example configured to calculate an estimated value of said concentration. The calculation of the estimated value is for example done using a calibration relationship previously determined, the calibration relationship defining a mathematical relationship between the intensity and the concentration. In other words, each intensity value is associated with a value of the concentration via this mathematical calibration relationship, for a predefined range of values of the concentration or intensity. The estimating software 60 is then configured for determining the value of the intensity for the considered pixels of the acquired image, then calculating the corresponding value of the concentration via the predetermined calibration relationship.

Additionally or alternatively, the estimating software 60 is configured to calculate an estimated variation of said concentration, said estimated variation being calculated by comparing the pixel intensity of the acquired image with that of a reference image, the reference image being chosen from among a predetermined image and an image of the culture medium previously acquired. The estimating software 60 is then configured for determining the value of the intensity for the considered pixels of the acquired image and that for the considered pixels of the reference image, then calculating the difference between these two intensity values, and lastly estimating the variation of the concentration from the calculated intensity difference.

The intensity taken into account to calculate this estimate is for example a mean value or a median value of the intensity of the considered pixels. A mean value refers to a value calculated in the form of an arithmetic mean, a geometric mean, a harmonic mean, a quadratic mean or a weighted mean. In general, the intensity taken into account to calculate this estimate is obtained by combining the intensity of each considered pixel of the acquired image. A considered pixel refers to a pixel of the acquired image whose intensity is taken into account to calculate the estimate of the concentration of the species in the culture medium, not all of the pixels of the acquired image necessarily being taken into account for this calculation, as will be described below.

The intensity is for example expressed in gray level when the acquired image is monochromatic.

As an optional addition, the estimating software 60 is configured to identify at least one elementary diffraction pattern 50 in the acquired image, then to select pixels situated outside each identified elementary diffraction pattern 50, and lastly to calculate the estimate of the concentration of the species in the culture medium 12 based on the intensity of the pixels thus selected.

Calculating the estimate of the concentration from the intensity of pixels situated outside each elementary diffraction pattern 50 makes it possible to obtain a better estimate of the concentration. Indeed, during the calibration, during which the mathematical relationship between the intensity and the concentration is predefined, the culture medium used to perform this calibration generally has no biological particles.

In order to identify at least one elementary diffraction pattern 50, the estimating software 60 is configured for locating a particular point, such as the center, of each elementary diffraction pattern 50 in the acquired image $I_n$. The location of each particular point, such as the center, is for example done by applying an autocorrelation function, preferably normalized, so as to obtain, from the acquired image and a reference elementary diffraction pattern $I_R$, a correlation image $I_C$, verifying the following equation:

$$I_C(x, y) = \frac{\sum_{i,j} I_R(i, j) \times I_n(x+i, y+j)}{\sqrt{\sum_{i,j} I_R(i, j)^2 \times \sum_{i,j} I_n(x+i, y+j)^2}} \quad (1)$$

In the correlation image $I_C$, each intensity peak then corresponding to the position of the center of the diffraction pattern corresponding to the reference image $I_R$.

The reference elementary diffraction pattern $I_R$ is established previously, based on a model or based on experimental images.

Alternatively, to detect the center of the diffraction pattern, the estimating software 60 is configured for reconstructing an image of the diffracting particles 32 from the acquired image $I_n$, and using a known holographic reconstruction algorithm. Such an algorithm makes it possible to reconstruct the geometry and/or the position of the diffracting object from an elementary diffraction pattern. The estimating software 60 is next able to detect the position corresponding to the center of each diffraction figure in the reconstructed image, then to determine a region of the acquired image $I_n$, this region including the corresponding elementary diffraction pattern 50.

Alternatively, the identification of at least one elementary diffraction pattern 50 is done manually, the operator performing a manual selection of the zone of the image that is considered to be representative of the corresponding elementary diffraction FIG. 50.

As an optional addition, the estimating software 60 is configured to calculate an estimate of the concentration from the intensity of the pixels of a zone of interest selected previously, the selected zone of interest preferably including at least one elementary diffraction pattern 50. Also preferably, the selected zone of interest includes a plurality of elementary diffraction patterns 50. The zone of interest is selected manually by the operator, or directly by the estimating software 60.

When both of the optional additions described above are implemented, the estimating software 60 is then configured to identify the or each elementary diffraction pattern 50 within the selected zone of interest, then to select, from among the pixels of the selected zone of interest, pixels situated outside each identified elementary diffraction pattern, and lastly to calculate the estimate of the concentration of the species in the culture medium 12 from the intensity of the pixels thus selected within the zone of interest.

Also as an optional addition, the estimating software 60 is configured to identify one or several elementary diffraction patterns 50 in the acquired image, then to determine a characteristic relative to each biological particle 32 corresponding to a respective identified elementary pattern.

A characteristic relative to the biological particles 32 refers to the count of biological particles 32, i.e., the count of the identified elementary diffraction patterns 50. This makes it possible to use the same acquired image to check both the concentration of the species in the medium and the cell proliferation, when the biological particles 32 are cells. In order to count the elementary diffraction patterns 50, the estimating software 60 is, as previously described, configured for locating a particular point, such as the center, of each elementary diffraction FIG. 50 in the acquired image $I_n$, then counting the number of said particular points in the acquired image $I_n$.

A characteristic relative to the biological particles 32 also refers to the identification of the biological particles 32 from the shape of the elementary diffraction pattern 50, the biological particles 32 being cells (red blood cells, white blood cells or platelets) or aggregates of cells, or bacteria or bacterial colonies. To identify the biological particles 32 corresponding to a given elementary diffraction pattern 50, the estimating software 60 is for example configured for carrying out a reconstruction algorithm for the optical properties of the biological particles 32, according to that described in document WO 2014/009519 A1 published on Jan. 16, 2014, in particular from page 8, line 31 to page 18, line 24. Optical properties of the biological particles 32 in particular refer to the absorption of the object or the phase delay introduced by the biological particles 32, knowing that these parameters respectively represent the modulus and the argument of the complex opacity function of the biological particle 32. The reconstruction algorithm in particular makes it possible to determine the spatial distribution of these parameters. When the biological particles 32 are cells, the estimating software 60 is then also configured for determining dimensions of the nucleus and/or cytoplasm of the cell, by implementing this reconstruction algorithm.

Figure 3:
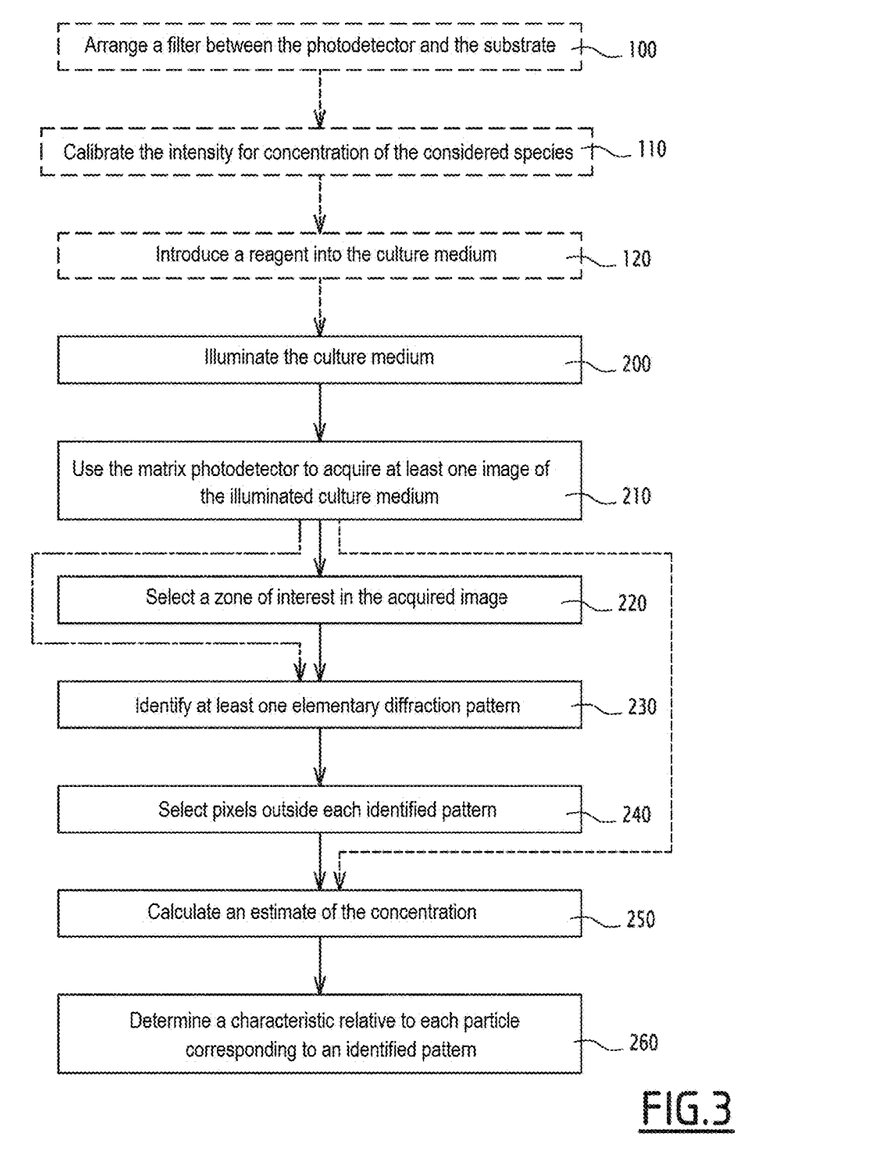
FIG. 3 is a flowchart of an estimating method according to the invention.

The operation of the estimating system 10 according to the invention will now be described using FIG. 3, showing a flowchart of the estimating method according to the invention.

Steps 100 to 120 are optional preliminary steps which, when implemented, are preferably done before placing the culture medium 12 on the transparent substrate 14.

Step 100 consists of arranging the optical filter 25 between the matrix photodetector 18 and the transparent substrate 14 in the vertical direction Z. The optical filter 25, placed between the transparent substrate 14 and the photodetector 18, then transmits only certain wavelengths that are predefined from the estimated concentration.

Step 110 is a step for calibrating the intensity for the considered concentration, during which the mathematical relationship between the intensity and the concentration is predefined, this relationship associating a value of the concentration with each intensity value, and for a predefined range of values of the concentration or intensity.

During the calibration step 110, the value of the concentration of the species in the calibration medium is modified according to different successive values, and the relationship between the intensity and the concentration is determined for these different successive values. The calibration medium is preferably provided with no biological particles, so that the relationship thus determined between the intensity and the concentration does not depend on the nature, i.e., the type, of the biological particles.

Figure 6:
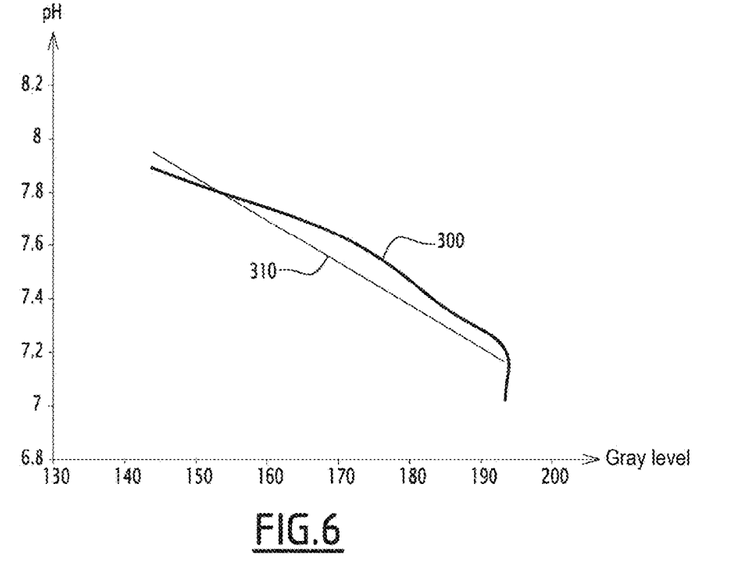
FIG. 6 is a curve obtained during a preliminary calibration step and showing the pH as a function of the intensity, expressed in gray levels, of the image of a calibration medium.

In the example of FIG. 6, the considered concentration is the pH (concentration of $H_3O^+$ ions), and a first curve 300 corresponds to intensity values expressed in gray levels, which are measured for images successively acquired as the pH of the calibration medium varies. The variation of the pH of the calibration medium is for example obtained by adding vinegar to the calibration medium, the value of the pH then being measured by impedance measurement. As an example, the gradual addition of 20 μL of vinegar to 3 ml of calibration medium makes it possible to vary the pH from an initial value substantially equal to 7.9 to a final value substantially equal to 7. From these measured values of the pH of the calibration medium, associated with measured intensity values, a mathematical relationship between the intensity and the pH, called calibration relationship, is determined. In the example of FIG. 6, this calibration relationship is obtained by interpolation from the first curve 300, and is shown in the form of a second curve 310. This relationship is for example a linear relationship, according to an order 1 interpolation, as shown in FIG. 6. One skilled in the art will of course understand that the calibration relationship is not necessarily a linear relationship, the interpolation making it possible to obtain this calibration relationship alternatively being of an order greater than or equal to 2.

When the estimated concentration is a ROS concentration, the calibration relationship is for example obtained for hydrogen peroxide $H_2O_2$ by measuring the absorption of the culture medium and the reagent without cells during the addition of a predefined quantity of $H_2O_2$ according to a range.

During the following preliminary step 120, the reagent is optionally introduced into the culture medium 12 to obtain, if applicable, the color change when the concentration varies. The reagent is for example phenol red to obtain a color change when the pH varies. As an illustrative example, the obtained color is then yellow for a pH below 6.6; red for a pH above 8.4; and orange (varying between yellow and red) in a turning point zone for a pH value comprised between 6.6 and 8.4.

When the estimated concentration is the cell viability (concentration of live cells), the reagent is for example MTS, and an absorbance variation will for example be observed at substantially 490 nm.

When the estimated concentration is a ROS concentration, such as hydrogen peroxide ($H_2O_2$), the reagent is for example (10-acetyl-3,7-dihydroxyphenoxazine), also called Amplex Red®, and an absorbance variation will for example be observed at substantially 560 nm.

At the end of the preliminary and optional steps 100 to 120, the culture medium 12 is, during step 200, placed on the transparent substrate 14, then illuminated by the light source 16. The culture medium 12 for example has a volume substantially equal to 3 ml. The culture medium 12 is for example a Dulbecco's Modified Eagle Medium (DMEM).

During the following step 210, the matrix photodetector 18 acquires the transmission image $I_n$ at moment $t_n$. As an optional addition, when the estimate of the concentration consists of estimating a variation of said concentration, the matrix photodetector 18 performs, during this step, the sequential acquisition of several transmission images $I_n$, $I_{n+1}$ at successive moments $t_n$, $t_{n+1}$.

Each transmission image $I_n$, $I_{n+1}$ is formed by the radiation transmitted, at the corresponding acquisition moment $t_n$, $t_{n+1}$, by the illuminated culture medium 12. In other words, the matrix photodetector 18 produces images of the elementary diffraction patterns 50 transmitted by the particles found in the illuminated culture medium 12, each elementary diffraction pattern corresponding to waves diffracted by the diffracting biological particles 32 during illumination of the culture medium 12, these diffracted waves interfering with the incident light wave.

The observation of a usable diffraction pattern, by placing the matrix photodetector 18 at a relatively small distance, is in particular due to the absence of a magnifying lens between the culture medium 12 and the matrix photodetector 18.

During the acquisition step 210, the photodetector 18 is preferably positioned at a small distance from the medium 12, the second distance D2 between the medium 12 and the photodetector 18 in the vertical direction Z generally being smaller than 5 cm, preferably smaller than 1 cm, and for example around several millimeters.

At the end of the acquisition step 210, the estimating software 60 selects, during the optional step 220, a zone of interest 320 in the acquired image(s) $I_n$, $I_{n+1}$, the selected zone of interest 320 preferably including at least one elementary diffraction pattern 50, more preferably a plurality of elementary diffraction patterns 50. Alternatively, the selection of the zone of interest 320 is done manually by the operator.

The selected zone of interest 320 is generally rectangular, each side of the rectangle having dimensions of about several tens or several hundreds of pixels, as shown in FIGS. 4 and 5.

Furthermore, in FIGS. 4 and 5, the line 330 corresponds to a border between a first zone 340 of the culture medium having a high cell proliferation and a second zone 350 of the culture medium having a low cell proliferation.

At the end of the acquisition step 210 (path in mixed lines in FIG. 3), or if applicable at the end of the optional selection step 220 (path in solid lines in FIG. 3), the estimating software 60 identifies, during the optional step 230, one or several elementary diffraction patterns 50, if applicable within the selected zone of interest. For example, the estimating software 60 locates a particular point, such as the center, of each elementary diffraction pattern 50 in the acquired image $I_n$, or if applicable in the selected zone of interest.

At the end of this optional identification step 230, the estimating software 60 selects, during the optional step 240, pixels of the acquired image $I_n$, or if applicable of the selected zone of interest, that are situated outside each identified elementary diffraction pattern.

The following step 250 for calculating the estimate of the concentration of the species in the culture medium 12 is carried out directly at the end of the acquisition step 210, as shown by the path in dotted lines in FIG. 3, or at the end of the optional pixel selection step 240, as shown by the path in solid lines in FIG. 3.

One skilled in the art will then understand that steps 220, 230 and 240 are optional to calculate the estimate of the concentration, these steps seeking to obtain a more precise estimate of the concentration by selecting only one zone of interest in the acquired image $I_n$ and/or by selecting pixels outside each identified elementary diffraction pattern, to next estimate the concentration of the species in the culture medium 12 based on the intensity of the pixels in said zone and/or selected outside each identified elementary diffraction pattern.

During step 250, the estimating software 60 begins by calculating a reference value of the intensity from:
  i) intensity values of pixels from the entire acquired image $I_n$ when steps 220, 230 and 240 are not carried out; or
  ii) intensity values of pixels from the selected zone of interest when only step 220 is carried out from among the optional steps 220 to 240; or
  iii) intensity values of pixels selected from the acquired image $I_n$ outside each identified elementary diffraction pattern, when only step 230 and 240 are carried out from among the optional steps 220 to 240; or
  iv) intensity values of pixels selected in the selected zone of interest and outside each identified elementary diffraction pattern, when all of the optional steps 220, 230 and 240 are carried out.

The reference value is for example a mean value (arithmetic, geometric, harmonic, quadratic or weighted) or a median value of said considered pixel intensity values. In general, this reference value is obtained by combining said considered pixel intensity values.

When the estimating software 60 is configured to calculate an estimated value of said concentration, this estimated value is then calculated by determining, via the calibration relationship, the value of the concentration corresponding to the reference value of the intensity previously calculated.

When the estimating software 60 is configured to calculate an estimated variation of said concentration, this estimated variation is calculated from the evolution between the reference values of the intensity calculated for at least two successive acquired images $I_n$, $I_{n+1}$, and according to the considered concentration.

In the example of FIG. 6, the pH decreases when the intensity, expressed in gray levels, increases. Thus, according to this example of FIG. 6, if the reference value of the intensity increases from one acquired image $I_n$ to the next $I_{n+1}$, then the estimating software 60 deduces a decrease in the pH of the culture medium 12 therefrom; conversely, if the reference value decreases from one acquired image $I_n$ to the next $I_{n+1}$, then the estimating software 60 deduces an increase in the pH therefrom; and if the reference value is substantially equal from one acquired image $I_n$ to the next $I_{n+1}$, then the estimating software 60 deduces a stabilization of the pH therefrom.

Figure 7:
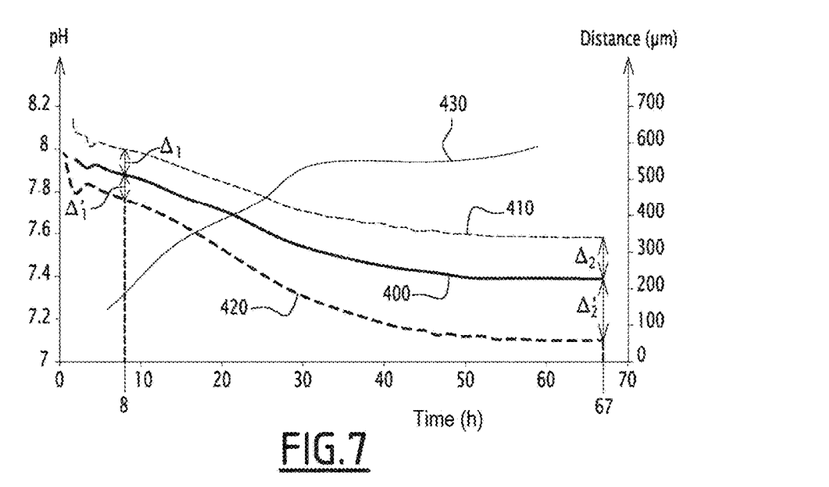
FIG. 7 is a set of curves, among which three first curves show the evolution over time of estimates of the pH for different pixel selections, and a fourth curve shows the evolution over time of a cell edge, the cell edge forming a boundary between a first portion of the culture medium with a low cell proliferation and a second portion of the culture medium with a high cell proliferation.

In the example of FIG. 7, the estimating software 60 has then made it possible to obtain first, second and third pH curves 400, 410 and 420. The first pH curve 400 (in thick solid lines) corresponds to the estimate of the pH from the intensity values of pixels from all of each acquired image $I_n$, i.e., when the intensity reference value for each acquired image $I_n$ is calculated according to case i). The second pH curve 410 (in thin dotted lines) corresponds to the estimate of the pH from the intensity values of pixels within the selected zone of interest for each acquired image $I_n$, but without selecting the pixels outside the elementary diffraction patterns 50, i.e., when the intensity reference value for each acquired image $I_n$ is calculated according to case ii). Lastly, the third pH curve 420 (in thick dotted lines) corresponds to the estimate of the pH from the intensity values of pixels within the selected zone of interest and outside the identified elementary diffraction patterns, i.e., when the intensity reference value for each acquired image $I_n$ is calculated according to case iv).

FIG. 7 then shows that the pH with the second curve 410 is greater than that with the first curve 400, which in turn is greater than that with the third curve 420. This is due to the fact that, for the example of FIG. 7, the calibration relationship has been determined from a calibration medium with no biological particles, and the third curve 420 that was obtained from pixels selected outside the elementary diffraction patterns is then the curve for which the estimated value of the pH is most reliable. The deviation with respect to the third curve 420 is logically greater for the second curve 410, obtained from the zone of interest selected around elementary diffraction patterns, while keeping these diffraction patterns, than for the first curve 400, which was obtained from pixels from all of each acquired image $I_n$.

This being said, one skilled in the art will note that a first relative pH deviation Δ between the first curve 400 and the second curve 410 varies little over the course of the evolution of the pH, and similarly, that a second relative pH deviation Δ' between the first curve 400 and the third curve 420 also varies little during the evolution of the pH. Indeed, a first value $\Delta_1$ of the first relative deviation is substantially equal to 0.12 at moment T0+8 h, and a first value $\Delta'_1$ of the second relative deviation is also substantially equal to 0.12 at this moment T0+8 h corresponding to the acquisition moment of the image $I_{n1}$ shown in FIG. 4, where T0 represents the initial moment of the test corresponding to FIGS. 4, 5 and 7. A second value $66_2$ of the first relative deviation is substantially equal to 0.20 at moment T0+67 h, and a second value $\Delta'_2$ of the second relative deviation is substantially equal to 0.28 at this moment T0+67 h corresponding to the acquisition moment of the image $I_{n2}$ shown in FIG. 5. The variation of the first and second relative deviations Δ, Δ' according to the evolution of the pH is then acceptable, knowing that basing oneself on the third curve 420, the estimated value of the pH is substantially equal to 7.8 at moment T0+8 h, then substantially equal to 7.1 at moment T0+67 h.

In other words, although it is preferable to calculate the estimated value of the pH of the culture medium 12 from the third curve 420 with the intensity reference value calculated according to case iv) after carrying out optional steps 220 to 240, one skilled in the art will understand that the estimating software 60 is nevertheless able to calculate a satisfactory estimated value of the pH from the first curve 400 with the intensity reference value calculated according to case i), i.e., going directly from step 210 to step 250.

Furthermore, in order to obtain a more reliable estimated pH value, the estimating software 60 is additionally able to subtract a predefined value from the estimated value obtained from the first curve 400, in order to compensate the bias in the value of the pH introduced by the presence of the elementary diffraction patterns 50 corresponding to the biological particles 32, whereas the calibration relationship has been determined from a calibration medium without these biological particles.

At the end of the estimate calculating step 250, the estimating step 60 determines, during optional step 260, a characteristic relative to each particle corresponding to an elementary diffraction pattern identified during step 230. This then makes it possible to track both the evolution of the concentration of the species in the culture medium 12 and the evolution of the characteristic relative to the biological particles 32 contained in the culture medium. As an example, when determining the characteristics of these biological particles 32 consists of counting these biological particles 32 in the culture medium, it is then possible to check both the cell proliferation and the evolution of the concentration in the culture medium 12.

In the example of FIG. 7, the curve 430 (in thin solid lines) then shows the evolution over time of the distance between the border 330 and a reference point, not shown. The border between the first zone 340 with the high cell proliferation and the second zone 350 with the low cell proliferation represents a cell proliferation edge, and the curve 430 then shows the movement of the cell proliferation edge over time. The combination of the curve 430 with any one of the first, second and third curves 400, 410, 420 then makes it possible to correlate the cell activity with the evolution of the pH of the culture medium 12.

One can then see that the estimating method and system 10 according to the invention make it possible to calculate an estimate of the concentration of the species in the culture medium based on the pixel intensity of the acquired image, the culture medium 12 changing color when said concentration varies.

When the estimated concentration is the pH of the culture medium 12, monitoring the pH then makes it possible to monitor the growth conditions of the biological particles 32 contained in the culture medium. Indeed, the pH of the culture medium 12 evolves when the medium 12 becomes nutrient-depleted, and it is interesting to be able to monitor the nutrient level in the culture medium 12, knowing that nutrient depletion slows cell proliferation.

The invention claimed is:

1. A method for estimating a concentration of a species in a culture medium using an estimating system including a light source, a transparent substrate and a matrix photodetector, the transparent substrate being located between the light source and the matrix photodetector, the culture medium including biological particles and being able to change color when the concentration of the species varies, the method comprising:

placing the culture medium on the transparent substrate,
illuminating the culture medium using the light source,
acquiring an image of the culture medium using the matrix photodetector, each image being formed by a radiation transmitted by the illuminated culture medium and including at least one elementary diffraction pattern corresponding to waves diffracted by a biological particle when the culture medium is illuminated, and
calculating an estimate of the concentration of the species in the culture medium from a pixel intensity of the acquired image, the estimate of the concentration being an estimated value of said concentration, the estimated value being calculated using a calibration relationship previously determined, the calibration relationship defining a mathematical relationship between the intensity and the concentration.

2. The method according to claim 1, wherein the acquired image is monochromatic.

3. A method for estimating a concentration of a species in a culture medium using an estimating system including a light source, a transparent substrate and a matrix photodetector, the transparent substrate being located between the light source and the matrix photodetector, the culture medium including biological particles and being able to change color when the concentration of the species varies, the method comprising:
placing the culture medium on the transparent substrate, illuminating the culture medium using the light source, acquiring an image of the culture medium using the matrix photodetector, each image being formed by a radiation transmitted by the illuminated culture medium and including at least one elementary diffraction pattern corresponding to waves diffracted by a biological particle when the culture medium is illuminated, and
calculating an estimate of the concentration of the species in the culture medium from a pixel intensity of the acquired image, the estimate of the concentration being an estimated variation of said concentration, said estimated variation being calculated by comparing the pixel intensity of the acquired image with that of a reference image, the reference image being chosen from among a predetermined image and an image of the culture medium previously acquired.

4. The method according to claim 1, wherein the light source illuminates the transparent substrate directly, and the image is formed directly by the radiation transmitted by the illuminated transparent substrate, in the absence of a magnification lens positioned between the transparent substrate and the matrix photodetector.

5. The method according to claim 1, wherein the concentration is chosen from among the group consisting of: pH, cell viability and ROS.

6. The method according to claim 1, wherein before acquiring an image of the culture medium, the method further comprises introducing a reagent into the culture medium to obtain a color change when the concentration varies.

7. The method according to claim 1, wherein after acquiring an image of the culture medium, the method further comprises:
identifying at least one elementary diffraction pattern in the acquired image, and
selecting pixels located outside each identified elementary diffraction pattern,
the estimate of the concentration of the species in the culture medium then being calculated, during calculating the concentration estimate, from the intensity of the selected pixels.

8. The method according to claim 1, wherein after acquiring an image of the culture medium, the method further comprises:
selecting a zone of interest in the acquired image,
the estimate of the concentration of the species in the culture medium then being calculated, during calculating the concentration estimate, from the intensity of the pixels of the selected zone of interest.

9. The method according to claim 8, wherein after acquiring an image of the culture medium, the method further comprises:
identifying at least one elementary diffraction pattern in the acquired image, and
selecting pixels located outside each identified elementary diffraction pattern,
the estimate of the concentration of the species in the culture medium then being calculated, during calculating the concentration estimate, from the intensity of the selected pixels, and
wherein selecting the zone of interest is carried out before said identifying,
identifying the or each elementary diffraction pattern then being done in the selected zone of interest,
the selection of pixels located outside each identified elementary diffraction pattern being done from among the pixels of the selected zone of interest, and
the estimate of the concentration of the species in the culture medium then being calculated from the intensity of said selected pixels.

10. The method according to claim 1, wherein the method further comprises a preliminary calibration, during which a relationship between the intensity of the concentration is determined using a calibration medium having a given value of the concentration.

11. The method according to claim 10, wherein, during the calibration, the value of the concentration of the species in the calibration medium is modified according to different successive values, and the relationship between the intensity and the concentration is determined for the different successive values.

12. The method according to claim 1, wherein before acquiring an image of the culture medium, the method further comprises:
placing a filter between the matrix photodetector and the transparent substrate, the filter being able to transmit only a predefined range of wavelengths.

13. The method according to claim 1, wherein after acquiring an image of the culture medium, the method further comprises:
identifying at least one elementary diffraction pattern in the acquired image, and
determining a characteristic relative to each biological particle corresponding to a respective identified elementary pattern.

14. The method according to claim 1, wherein the intensity taken into account during calculating the concentration estimate is a mean value or a median value of the intensity of the considered pixels.

15. The method according to claim 3, wherein after acquiring an image of the culture medium, the method further comprises:
selecting a zone of interest in the acquired image,
the estimate of the concentration of the species in the culture medium then being calculated, during calculating the concentration estimate, from the intensity of the pixels of the selected zone of interest.

16. The method according to claim 15, wherein after acquiring an image of the culture medium, the method further comprises:
identifying at least one elementary diffraction pattern in the acquired image, and
selecting pixels located outside each identified elementary diffraction pattern,
the estimate of the concentration of the species in the culture medium then being calculated, during calculating the concentration estimate, from the intensity of the selected pixels, and
wherein selecting the zone of interest is carried out before said identifying, identifying the or each elementary diffraction pattern then being done in the selected zone of interest, the selection of pixels located outside each identified elementary diffraction pattern being done from among the pixels of the selected zone of interest, and the estimate of the concentration of the species in the culture medium then being calculated from the intensity of said selected pixels.

17. A system for estimating a concentration of a species in a culture medium, the culture medium including biological particles and being able to change color when the concentration of the species varies, the system comprising:

a transparent substrate configured for receiving the culture medium, a light source configured for emitting a light beam illuminating the culture medium, a matrix photodetector configured for acquiring an image of the culture medium, each image being formed by a radiation transmitted by the illuminated culture medium and including at least one elementary diffraction pattern corresponding to waves diffracted by a biological particle when the culture medium is illuminated, the transparent substrate being located between the light source and the matrix photodetector, and an information processing unit configured for calculating an estimate of the concentration of the species in the culture medium from a pixel intensity of the acquired image, the estimate of the concentration being an estimated value of said concentration, the estimated value being calculated using a calibration relationship previously determined, the calibration relationship defining a mathematical relationship between the intensity and the concentration.

18. A system for estimating a concentration of a species in a culture medium, the culture medium including biological particles and being able to change color when the concentration of the species varies, the system comprising:

a transparent substrate configured for receiving the culture medium, a light source configured for emitting a light beam illuminating the culture medium, a matrix photodetector configured for acquiring an image of the culture medium, each image being formed by a radiation transmitted by the illuminated culture medium and including at least one elementary diffraction pattern corresponding to waves diffracted by a biological particle when the culture medium is illuminated, the transparent substrate being located between the light source and the matrix photodetector, and an information processing unit configured for calculating an estimate of the concentration of the species in the culture medium from a pixel intensity of the acquired image, the estimate of the concentration being an estimated variation of said concentration, said estimated variation being calculated by comparing the pixel intensity of the acquired image with that of a reference image, the reference image being chosen from among a predetermined image and an image of the culture medium previously acquired.

19. The method according to claim 3, wherein the concentration is chosen from among the group consisting of pH, cell viability and ROS.

20. The method according to claim 3, wherein after acquiring an image of the culture medium, the method further comprises:

identifying at least one elementary diffraction pattern in the acquired image, and selecting pixels located outside each identified elementary diffraction pattern, the estimate of the concentration of the species in the culture medium then being calculated, during calculating the concentration estimate, from the intensity of the selected pixels.

* * * * *